United States Patent
Takeda et al.

(10) Patent No.: US 9,878,116 B2
(45) Date of Patent: Jan. 30, 2018

(54) LARYNGEAL MASK

(75) Inventors: Yoshimasa Takeda, Okayama (JP);
Kiyoshi Morita, Okayama (JP);
Hiroshi Hashimoto, Izumi (JP);
Masatomo Kokubu, Izumi (JP)

(73) Assignees: DAIKEN IKI KABUSHIKI KAISHA, Osaka-shi, Osaka (JP); NATIONAL UNIVERSITY CORPORATION OKAYAMA UNIVERSITY, Okayama-shi, Okayama (JP)

( * ) Notice: Subject to any disclaimer, the term of this patent is extended or adjusted under 35 U.S.C. 154(b) by 255 days.

(21) Appl. No.: 14/122,813

(22) PCT Filed: May 22, 2012

(86) PCT No.: PCT/JP2012/003327
§ 371 (c)(1),
(2), (4) Date: Nov. 27, 2013

(87) PCT Pub. No.: WO2012/164868
PCT Pub. Date: Dec. 6, 2012

(65) Prior Publication Data
US 2014/0076309 A1    Mar. 20, 2014

(30) Foreign Application Priority Data
May 31, 2011    (JP) .................. 2011-121976

(51) Int. Cl.
*A61M 16/04*    (2006.01)
*A61F 7/12*    (2006.01)
(Continued)

(52) U.S. Cl.
CPC ......... *A61M 16/0434* (2013.01); *A61F 7/123* (2013.01); *A61M 16/0057* (2013.01);
(Continued)

(58) Field of Classification Search
CPC .......... A61M 16/0434; A61M 16/0497; A61M 16/1075; A61M 16/0488
(Continued)

(56) References Cited

U.S. PATENT DOCUMENTS 4,832,020 A    5/1989    Augustine
5,042,469 A    8/1991    Augustine
(Continued)

FOREIGN PATENT DOCUMENTS

CN    1441685    9/2003
CN    1863568    11/2006
(Continued)

OTHER PUBLICATIONS

European Appl. No. 12 793 620.1—Extended Search Report dated Feb. 5, 2015.
(Continued)

*Primary Examiner* — (Jackie) Tan-Uyen T Ho
*Assistant Examiner* — Margaret Luarca
(74) *Attorney, Agent, or Firm* — Gerald E. Hespos; Michael J. Porco; Matthew T. Hespos

(57) ABSTRACT

A laryngeal mask is provided with an outer tube and a connector, having a base end in which is formed a first connecting portion capable of being connected to an artificial respirator and a leading end in which is formed a ventilation opening, the outer tube and the connector having a communication passage formed therein that communicates between the first connecting portion and the ventilation opening, a ring-shaped cuff capable of tightly adhering to a tracheal opening of a patient trachea as a result of inflating in a state where the ring-shaped cuff is inserted to a predetermined insertion position, and hyoid bone-contacting portions and protruding laterally from the outer tube so as to contact from above a site in a pharyngeal portion of the
(Continued)

patient corresponding to a hyoid bone of the patient in a state where the ring-shaped cuff is inserted to the insertion position.

6 Claims, 9 Drawing Sheets

(51) Int. Cl.
 *A61M 16/00* (2006.01)
 *A61M 16/10* (2006.01)
(52) U.S. Cl.
 CPC .... *A61M 16/0409* (2014.02); *A61M 16/0415* (2014.02); *A61M 16/0438* (2014.02); *A61M 16/0445* (2014.02); *A61M 16/0488* (2013.01); *A61M 16/0497* (2013.01); *A61M 16/1075* (2013.01); *A61M 2205/3606* (2013.01); *A61M 2210/1028* (2013.01)
(58) Field of Classification Search
 USPC .......................... 128/200.26, 207.15, 205.15
 See application file for complete search history.

(56) References Cited

U.S. PATENT DOCUMENTS

| | | | |
|---|---|---|---|
| 5,203,320 A | | 4/1993 | Augustine |
| 6,070,581 A | | 6/2000 | Augustine et al. |
| 6,119,695 A | | 9/2000 | Augustine et al. |
| 6,604,525 B2 * | | 8/2003 | Pagan .................. A61M 16/04 128/207.14 |
| 2003/0172935 A1 | | 9/2003 | Miller |
| 2003/0213492 A1 | | 11/2003 | Alfery et al. |
| 2004/0089307 A1 | | 5/2004 | Brain |
| 2005/0066975 A1 | | 3/2005 | Brain |
| 2006/0124132 A1 | | 6/2006 | Brain |
| 2006/0180156 A1 | | 8/2006 | Baska |
| 2006/0276552 A1 * | | 12/2006 | Barbut ...................... A61F 7/12 514/743 |
| 2008/0086186 A1 | | 4/2008 | Takeda et al. |
| 2009/0177258 A1 | | 7/2009 | Takeda et al. |
| 2010/0126512 A1 | | 5/2010 | Nasir |
| 2011/0226256 A1 * | | 9/2011 | Dubach ................. A61M 16/04 128/207.14 |

FOREIGN PATENT DOCUMENTS

| | | |
|---|---|---|
| GB | 2331932 A | 9/1999 |
| JP | 64-15062 | 1/1989 |
| JP | H11206885 A | 8/1999 |
| JP | 2003-511108 | 3/2003 |
| JP | 2007-75505 | 3/2007 |
| JP | 2007-521044 | 8/2007 |
| WO | 2005/046751 | 5/2005 |

OTHER PUBLICATIONS

International Search Report dated Jul. 10, 2012.
Chinese Appl. No. 201280026532.1—Chinese Office Action dated Apr. 3, 2015.
Japanese Office Action Dated March 8, 2016.

* cited by examiner

LARYNGEAL MASK

BACKGROUND

Technical Field

The present invention relates to a laryngeal mask.

Background Art

Laryngeal masks for securing an airway in the human body while blocking communication between the esophagus and the trachea are known in the prior art. An explanation is first provided of the structure of the human body J with reference to FIG. 6.

The human body J has a nasal cavity J1, an oral cavity J2, a pharyngeal portion T communicated with the nasal cavity J1 and the oral cavity J2, and an esophagus J5 and a trachea J6 branching from this pharyngeal portion T. A first constricting portion J4, which is constricted by the action of a sphincter for establishing or blocking communication between the esophagus J5 and the pharyngeal portion T, is formed on the upstream side of the esophagus J5.

For example, a laryngeal mask described in Japanese Unexamined Patent Publication No. 2003-511108 is provided with an airway tube inserted into the body through the oral cavity J2, and a masking ring provided on the leading end of this airway tube. The masking ring has an elliptical shape and can be inflated and deflated. The leading end of the airway tube opens into an interior region of the masking ring, and an artificial respirator can be connected to the base end of the airway tube.

In the case of using the laryngeal mask of Japanese Unexamined Patent Publication No. 2003-511108, the airway tube is inserted into the body until the leading end of the deflated masking ring contacts the region of the sphincter (namely, the first constricting portion J4). In other words, a medical professional discontinues insertion of the laryngeal mask when a sensation is felt of the leading end of the masking ring having contacted the region of the sphincter. While in this state, the masking ring adheres tightly to the opening of the trachea J6 as a result of being inflated. As a result, communication between the esophagus J5 and the trachea J6 is blocked. In addition, while in this state, the trachea J6 is able to communicate with an artificial respirator through the airway tube that opens into the interior region of the masking ring. Thus, an airway can be secured while blocking communication between the esophagus J5 and the trachea J6.

However, in the case of using the laryngeal mask described in Japanese Unexamined Patent Publication No. 2003-511108, it is difficult to accurately secure an airway.

More specifically, the depth at which the laryngeal mask described in Japanese Unexamined Patent Publication No. 2003-511108 is inserted into the body is determined based on the presence or absence of the sensation felt when the leading end of the masking ring contacts the region of the sphincter (namely, the first constricting portion J4). Here, the region of the sphincter (the first constricting portion J4) is soft tissue and easily deformed. Consequently, it is difficult to accurately determine whether the masking ring has contacted the first constricting portion J4. Moreover, if the insertion site of the masking ring shifts from the target opening of the trachea J6, an airway cannot be accurately secured even if this masking ring is inflated.

SUMMARY OF THE INVENTION

An object of the present invention is to provide a laryngeal mask that allows an airway to be accurately secured by a simple procedure.

In order to solve the problems described above, the present invention provides a laryngeal mask for securing an airway of a patient, provided with: an insertion tube, having a base end in which is formed a connecting portion capable of being connected to an artificial respirator, a leading end in which is formed a ventilation opening, and a communication passage formed therein that communicates between the connecting portion and the ventilation opening, a ring-shaped cuff which is attached to the leading end of the insertion tube so as to surround the ventilation opening, and is capable of tightly adhering to a tracheal opening of a patient trachea as a result of inflating in a state where the ring-shaped cuff is inserted to a predetermined insertion position in the patient, and at least one hyoid bone-contacting portion that protrudes laterally from the insertion tube so as to contact a site, in a pharyngeal portion of the patient, corresponding to a hyoid bone of the patient in a state where the ring-shaped cuff is inserted to the insertion position.

According to the present invention, an airway can be accurately secured by a simple procedure.

DETAILED DESCRIPTION OF THE PREFERRED EMBODIMENTS

The following provides an explanation of embodiments of the present invention with reference to the attached drawings. These embodiments are merely examples of embodying the present invention, and are not intended to limit the technical scope thereof First, an explanation is provided of the structure of a human body J with reference to FIGS. 6 and 8. The human body J has a nasal cavity J1, an oral cavity J2, a pharyngeal portion T communicated with the nasal cavity J1 and the oral cavity J2, an esophagus J5 and a trachea J6 branching from this pharyngeal portion T, an epiglottis J3 provided in the pharyngeal portion T for inhibiting entry of food into the trachea J6, and a U-shaped hyoid bone J7 surrounding the pharyngeal portion T from the anterior side and both the left and right sides in the vicinity of this epiglottis J3. A first constricting portion J4, which is constricted by the action of a sphincter for establishing or blocking communication between the esophagus J5 and the pharyngeal portion T, is formed on the upstream side of the esophagus J5. The pharyngeal portion T has an upper pharyngeal portion T1, which is provided in the range of the pharyngeal portion T above the branch of the nasal cavity J1 and the oral cavity J2, a middle pharyngeal portion T2, which is provided in the range of the pharyngeal portion T extending from the upper pharyngeal portion T1 to the epiglottis J3, and a lower pharyngeal portion T3, which is provided in the range of the pharyngeal portion T below this middle pharyngeal portion T2.

The following provides an explanation of a preferred embodiment of the present invention with reference to the drawings.

Figure 9:
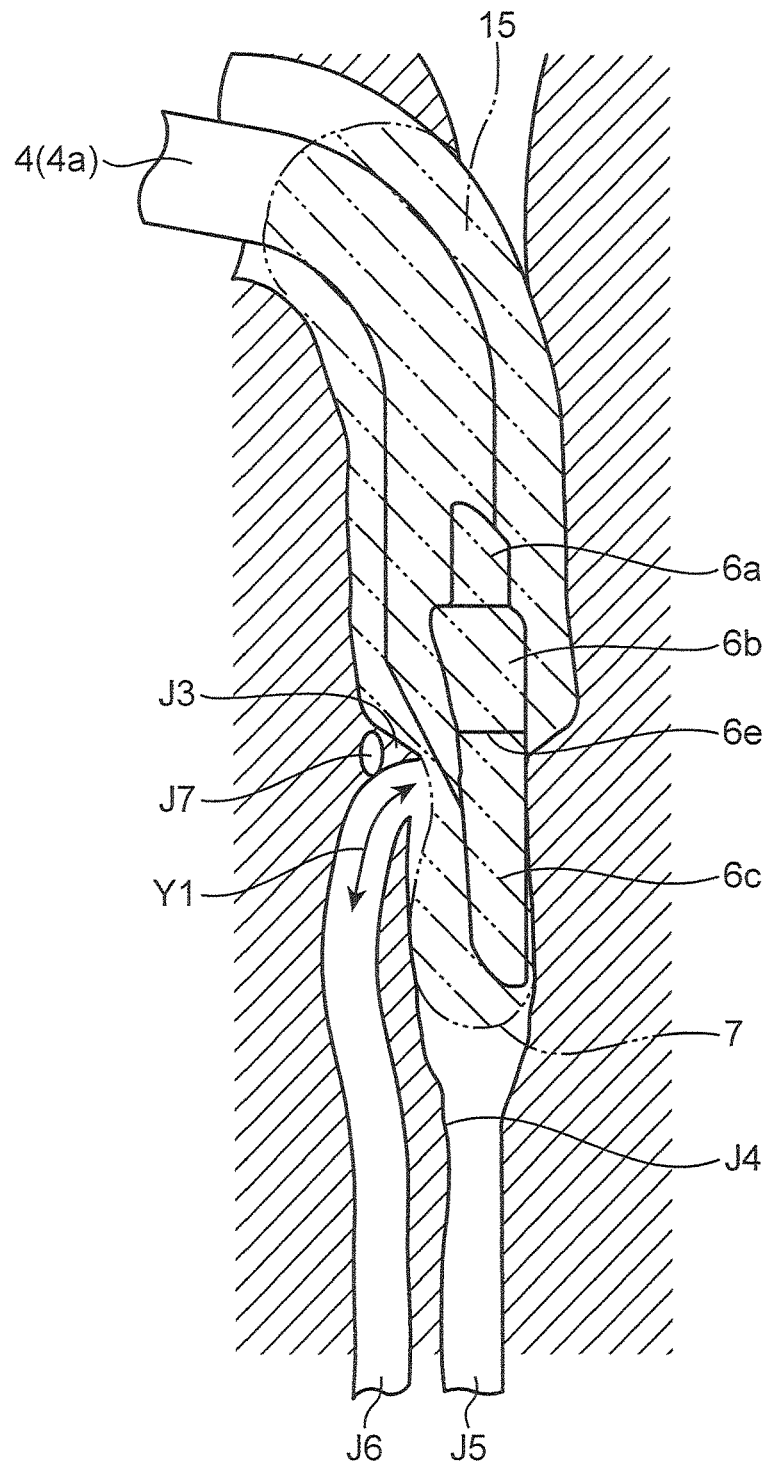
FIG. 9 is a side cross-sectional view showing the insertion tube shown in FIG. 5 inserted into a body, and a ring-shaped cuff in an inflated state.

As shown in FIG. 9, the laryngeal mask 1 according to the present embodiment is for securing an airway as indicated by arrows Y1 in a state where the esophagus J5 and the trachea J6 blocked by a ring-shaped cuff 7.

More specifically, as shown in FIGS. 1 to 4, the laryngeal mask 1 is provided with a mask body 2 for securing an airway in the human body J, and a cooling portion 3 for cooling the pharyngeal portion T of the human body.

The mask body 2 is provided with an insertion tube body 4 inserted into the body through the oral cavity J2 of the human body J, a connector 5 attached to the base end of the insertion tube body 4, a positioning member 6 for positioning the insertion depth of the insertion tube body 4 at a predetermined insertion position (see FIG. 7), and the ring-shaped cuff 7 attached to the leading end of the insertion tube body 4.

The insertion tube body 4 is provided with an outer tube 4a for securing an airway in the human body J, and an inner tube 4b inserted inside the outer tube 4a. The outer tube 4a is curved corresponding to the route from the oral cavity J2 to the esophagus J5 of the human body J. In addition, the leading end of the outer tube 4a is in the form of an inclined plane facing the inside of the curved shape (side in which the center of the curve is positioned) of the outer tube 4a. Moreover, a through hole is formed in the outer tube 4a and extends over the entire length in the lengthwise direction from the base end of the outer tube 4a to the leading end of the outer tube 4a. More specifically, the through hole communicates from the opening of the leading end to the opening of the base end of the outer tube 4a. The inner tube 4b is for aspirating obstructive substances present in the esophagus J5 of the human body J. More specifically, the inner tube 4b extends beyond the leading end of the outer tube 4a and penetrates the ring-shaped cuff 7 to be subsequently described.

The connector 5 is a Y-shaped tube for connecting an artificial respirator or aspirator and the like not shown to the insertion tube body 4. More specifically, the connector 5 is provided with a cylindrical body portion 5a installed on the base end of the outer tube 4a, and cylindrical first connecting portion 5b and second connecting portion 5c that protrude from this body portion 5a and communicate within the body portion 5a. The base end of the outer tube 4a is fit into the body portion 5a in an airtight state. The base end of the inner tube 4b introduced into the connector 5 through the body portion 5a is fit into the second connecting portion 5c in an airtight state. The first connecting portion 5b communicates with the space outside the inner tube 4b in a space within the through hole of the outer tube 4a. Thus, the space between the outer tube 4a and the inner tube 4b is connected with an artificial respirator not shown by connecting the artificial respirator to the first connecting portion 5b. On the other hand, the space within the inner tube 4b is connected with an aspirator not shown by connecting the aspirator to the second connecting portion 5c. The outer tube 4a and the connector 5 according to the present embodiment comprise an insertion tube that has a base end, in which is formed the first connecting portion 5b capable of connecting to an artificial respirator, and a leading end in which is formed a ventilation opening, and has a through hole formed therein that communicates between the first connecting portion 5b and the ventilation opening.

Figure 3:
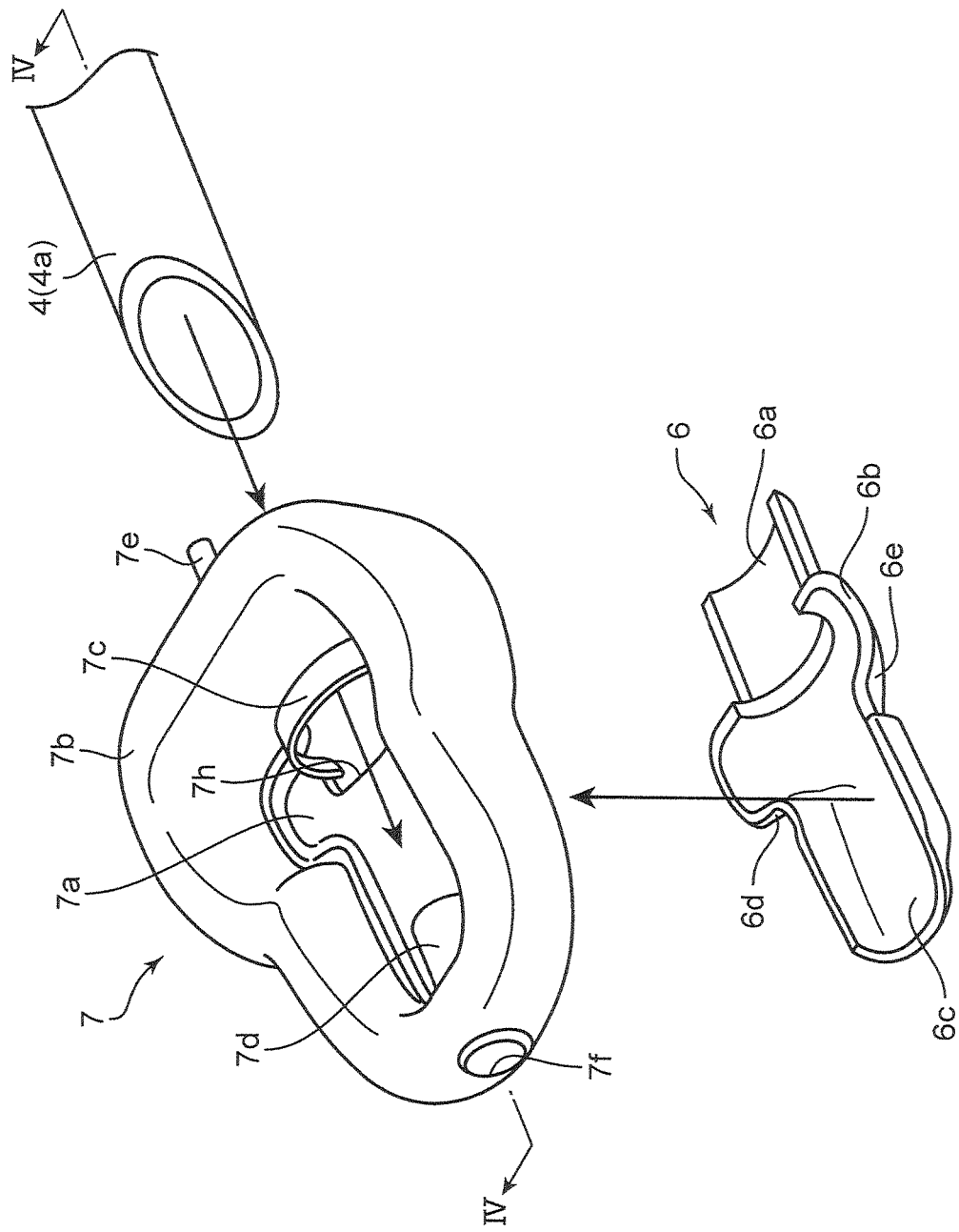
FIG. 3 is an exploded perspective view showing an enlargement of a portion of a mask body shown in FIG. 2.
Figure 4:
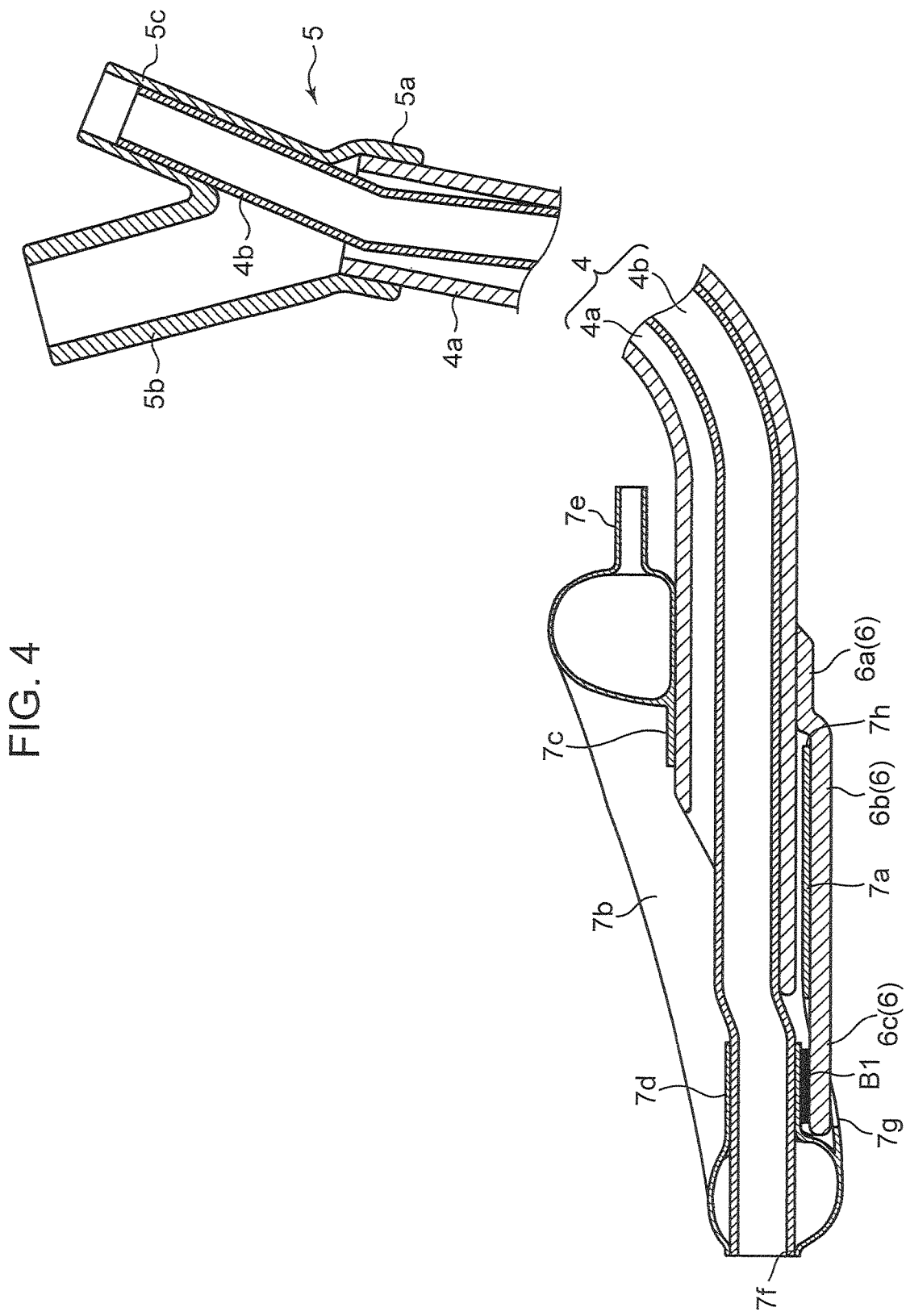
FIG. 4 is a cross-sectional view taken along line IV-IV of FIG. 3.
Figure 5:
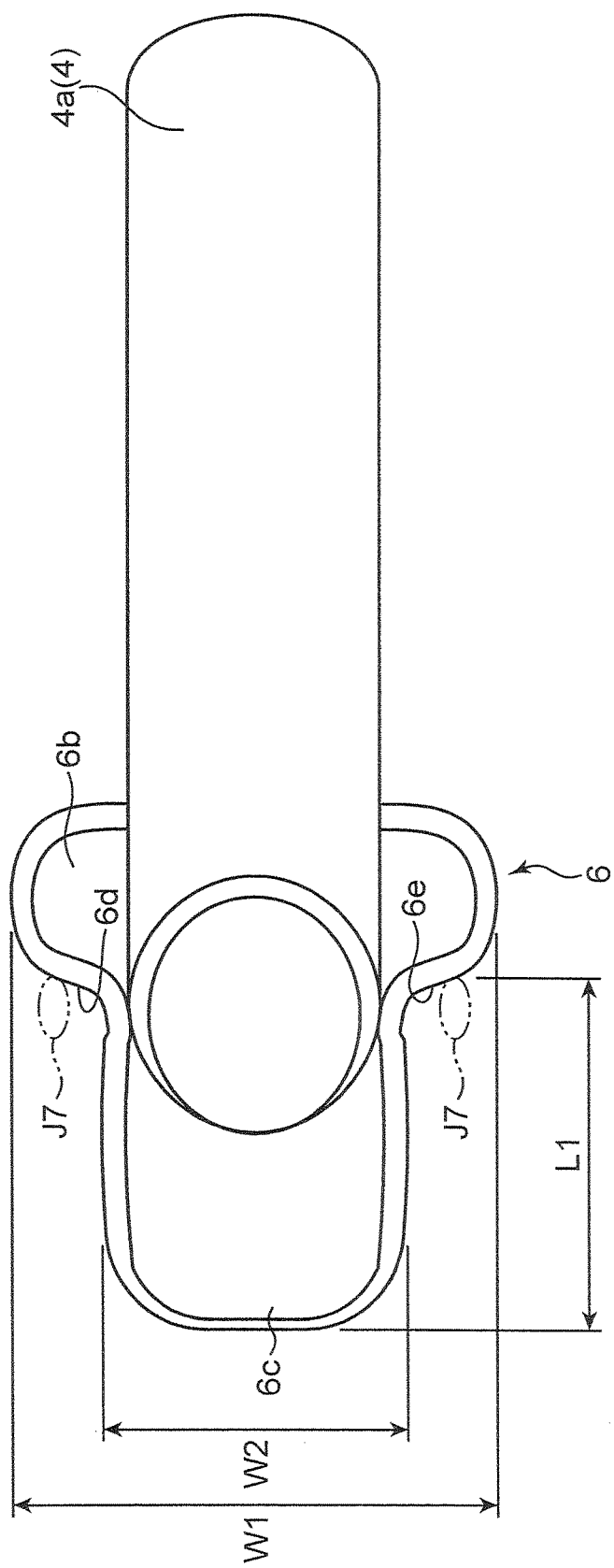
FIG. 5 is a plan view of FIG. 3 while omitting a portion thereof.
Figure 7:
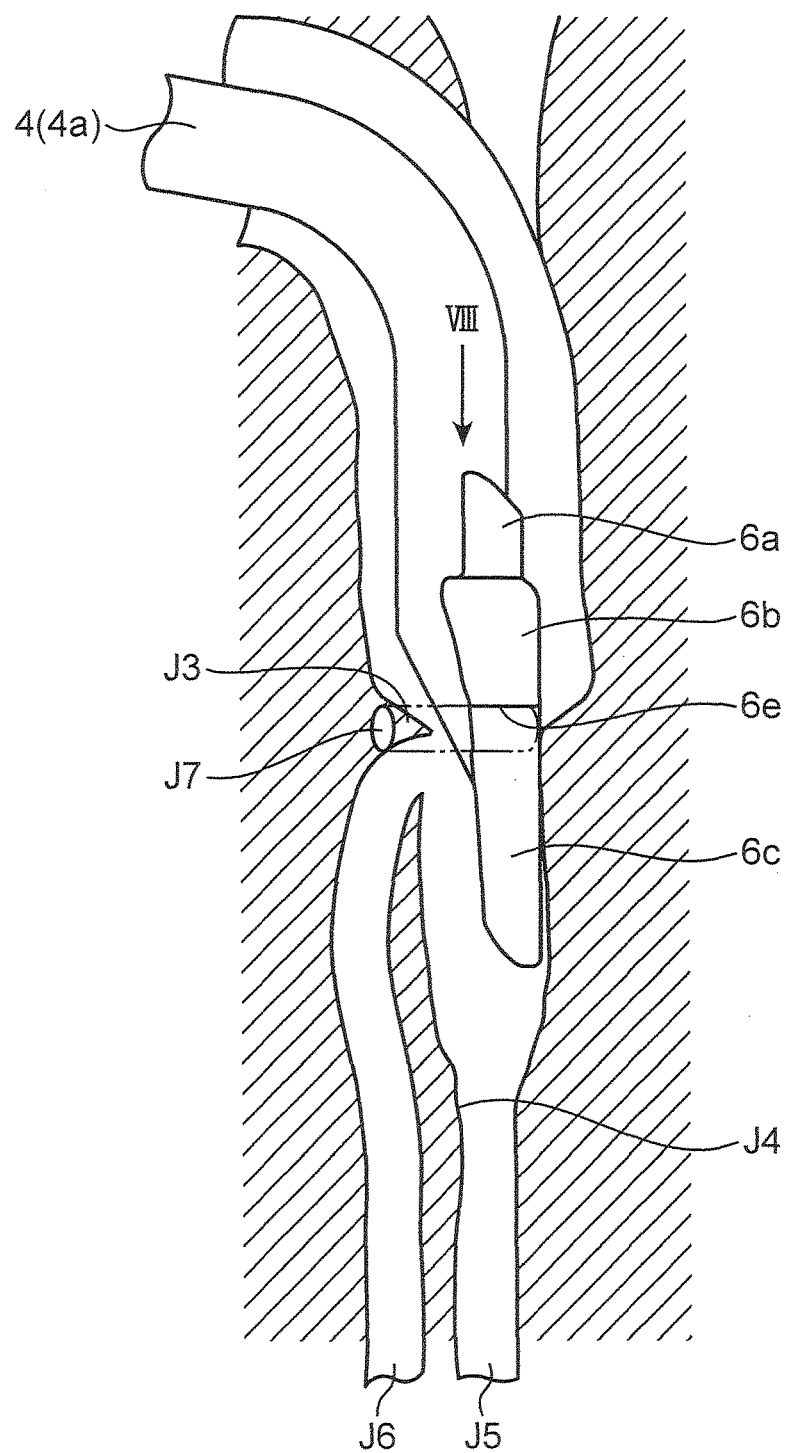
FIG. 7 is a side cross-sectional view showing the insertion tube shown in FIG. 5 inserted into the human body and a hyoid bone-contacting portion contacting the hyoid bone.

The positioning member 6 is able to contact from above a site, within the pharyngeal portion T of the human body J, corresponding to the hyoid bone J7 as shown in FIG. 7 in a state where the ring-shaped cuff 7 to be subsequently described is inserted to the insertion position shown in FIG. 9. More specifically, as shown in FIGS. 3 to 5, the positioning member 6 is provided with a tube connecting portion 6a connected to the outer tube 4a, a wide portion 6b provided on the leading end side of this tube connecting portion 6a, and an extending portion 6c extending from this wide portion 6b to the leading end side. The tube connecting portion 6a is formed into the shape of an arc having a radius of curvature that enables it to be arranged along the outer surface of the outer tube 4a. This tube connecting portion 6a is adhered to the outer surface of the outer tube 4a. The wide portion 6b has a width W1 larger than the diameter of the outer tube 4a (see FIG. 5). Both the left and right portions of this wide portion 6b protrude equally to the left and right from the outer tube 4a in a planer view. The extending portion 6c has a width W2 smaller than the wide portion 6b. More specifically, the extending portion 6c protrudes to the leading end side from the center position in a right-and-left direction of the wide portion 6b so that hyoid bone-contacting portions 6d and 6e respectively remain on the left and right sides of the wide portion 6b. In other words, in the present embodiment, the portions of the wide portion 6b that protrude in the direction of width (right-and-left direction) from the extending portion 6c configure the two left and right hyoid bone-contacting portions 6d and 6e having equal widths. These hyoid bone-contacting portions 6d and 6e are provided at positions able to contact a site corresponding to the hyoid bone J7 from above in a state where the ring-shaped cuff 7 to be subsequently described is inserted to a predetermined insertion position. More specifically, in the present embodiment, the hyoid bone-contacting portions 6d and 6e are respectively provided at the same positions in the lengthwise direction of the outer tube 4a. In addition, each of the hyoid bone-contacting portions 6d and 6e is provided at an interval that enables contact with portions on the left and right sides of a site corresponding to the hyoid bone J7 from above (this interval is about 40 mm in the present embodiment). The extending portion 6c is formed in the shape of a flat plate having a length L1 from the wide portion 6b. More specifically, the extending portion 6c extends to the leading end side beyond the leading end of the outer tube 4a. Consequently, the extending portion 6c can be slid into the narrow space between the epiglottis J3 and the posterior wall of the pharyngeal portion T even if the epiglottis J3 has descended as indicated by the double-dot broken line of FIG. 8.

Furthermore, among the outer tube 4a and the ring-shaped cuff 7 having hardness that is lower than that of the outer tube 4a, the positioning member 6 has hardness that is at least harder than the ring-shaped cuff 7. More specifically, the hardness of the positioning member 6 can be adjusted according to the material and dimensions thereof The ring-shaped cuff 7 can be tightly adhered to the tracheal opening of the trachea J6 by being inflated in a state where the ring-shaped cuff 7 is inserted to a predetermined insertion position as shown in FIG. 9. More specifically, as shown in FIGS. 1 to 4, the ring-shaped cuff 7 is provided with a bottom portion 7a in the shape of a flat plate corresponding to the positioning member 6 (wide portion 6b and extending portion 6c), a ring-shaped cuff body 7b provided over the entire periphery of the peripheral edge of this bottom 7a, an outer tube attaching portion 7c for attaching the outer tube 4a, inner tube attaching portions 7d and 7f for attaching the inner tube 4b, and a gas supply and evacuation portion 7e for supplying and evacuating a gas to and from the ring-shaped cuff body 7b. As shown in FIG. 4, a through hole 7g and a through hole 7h are formed in the bottom portion 7a. The outer tube 4a passes through the through hole 7h, and the opening in the leading end of the outer tube 4a is arranged substantially in the center of the ring-shaped cuff body 7b. The outer tube attaching portion 7c extends towards the leading end side from the lower portion of the base end side of the ring-shaped cuff body 7b and is adhered to the outer surface of the outer tube 4a. The inner tube 4b leading out from the outer tube 4a is adhered in an airtight state to the inner tube attaching portions 7d and 7f while passing through the leading end of the ring-shaped cuff body 7b. The inner tube attaching portions 7d and 7f respectively communicate with the inside of the ring-shaped cuff body 7b and are formed into the shape of a tube that enables the inner tube 4b to be inserted therein. The ring-shaped cuff body 7b is attached to the leading end of the outer tube 4a so as to surround the opening in the leading end of the outer tube 4a. In addition, the ring-shaped cuff body 7b can be inflated or deflated by supplying or evacuating a gas through the gas supply and evacuation portion 7e. An extension tube not shown and a supply and evacuation port not shown provided on the leading end of this extension tube are connected to the gas supply and evacuation portion 7e. In a state where the ring-shaped cuff body 7b has been inserted to a predetermined insertion position, the supply and evacuation port is led outside the human body J by the extension tube. The ring-shaped cuff body 7b is inflated or deflated by supplying or evacuating a gas to or from the ring-shaped cuff body 7b from outside the human body J through the gas supply and evaluation port.

A surface on one side of the ring-shaped cuff body 7b (top surface in FIG. 4) is able to tightly adhere to the tracheal opening of the trachea J6 over the entire periphery thereof. The ring-shaped cuff 7, the positioning member 6 and the outer tube 4a are fixed in an airtight state to allow the outer tube 4a and the trachea J6 to reliably communicate while in this tightly adhered state. More specifically, the tube connecting portion 6a of the positioning member 6 is adhered in an airtight state to the outer tube 4a positioned farther towards the base end side than the through hole 7h of the bottom portion 7a. The extending portion 6c of the positioning member 6 is introduced to the inside of the ring-shaped cuff body 7b through the through hole 7g, and is adhered in an airtight state to the outer surface of the inner tube attaching portion 7d. Those portions of the positioning member 6 other than the tube connecting portion 6a and the extending portion 6c are adhered in an airtight state to the ring-shaped cuff 7 and/or the outer tube 4a. In addition, in those portions not interposed by the positioning member 6, the ring-shaped cuff 7 is adhered in an airtight state to the outer tube 4a.

Furthermore, in the present embodiment, the extending portion 6c of the positioning member 6 is adhered to the inner tube attaching portion 7d and not the ring-shaped cuff body 7b. The reason for this is to allow the ring-shaped cuff body 7b to be reliably adhered to the lower pharyngeal portion T3 by avoiding interposition by the positioning member 6 between the posterior surface of the ring-shaped cuff body 7b and the lower pharyngeal portion T3 (first constricting portion). As a result, the esophagus J5 and the trachea J6 are able to be reliably blocked by the ring-shaped cuff body 7b.

Figure 1:
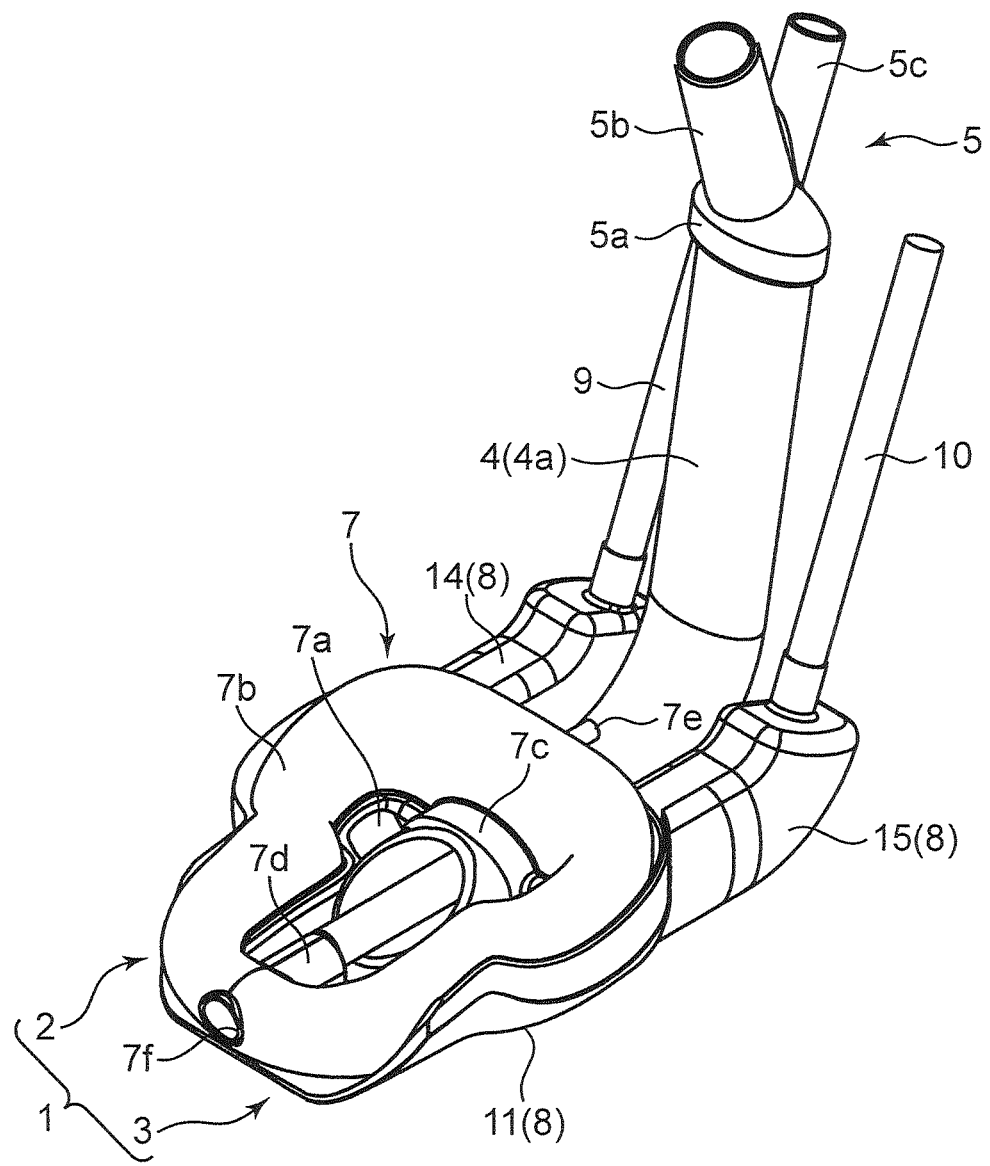
FIG. 1 is a perspective view showing the overall configuration of a laryngeal mask according to an embodiment of the present invention.
Figure 2:
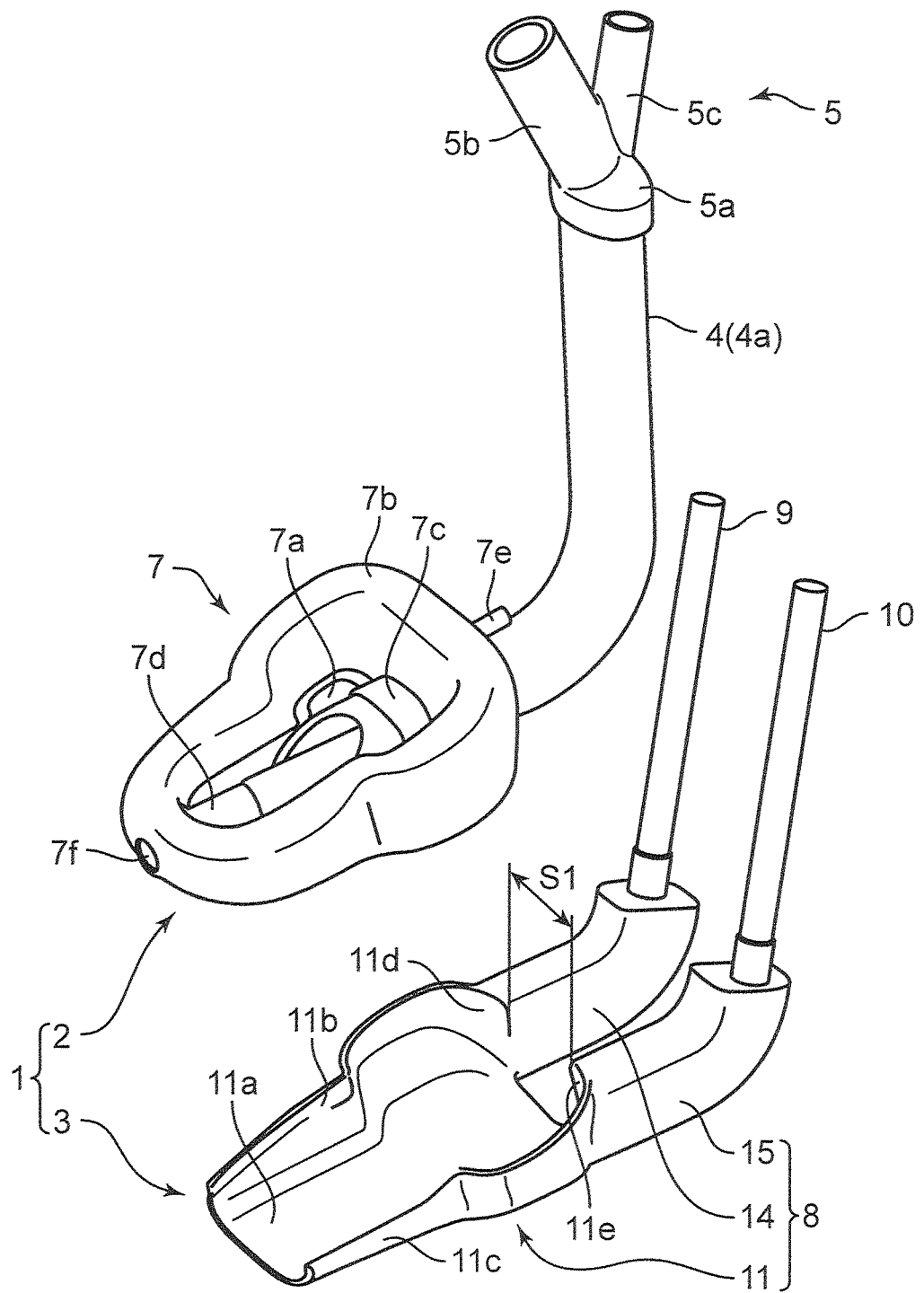
FIG. 2 is an exploded perspective view of the laryngeal mask shown in FIG. 1.

With reference to FIGS. 1 and 2, the cooling portion 3 is able to cool the pharyngeal portion T by tightly adhering to the pharyngeal portion T in a state where the ring-shaped cuff 7 is inflated. More specifically, the cooling portion 3 is provided with a cooling cuff 8, which inflates as a result of housing a coolant and deflates as a result of evacuating the coolant, and a pair of supply and evacuation tubes 9 and 10 capable of supplying and evacuating the coolant to and from this cooling cuff 8.

The cooling cuff 8 is able to inflate so as to tightly adhere to the posterior walls of the lower pharyngeal portion T3 and middle pharyngeal portion T2 (see FIG. 6) of the human body J in a state where the ring-shaped cuff 7 is inflated. More specifically, the cooling cuff 8 is provided with a fixing portion 11 in which the ring-shaped cuff 7 is fixed, and a pair of left and right extending portions 14 and 15 extending towards the base end side from this fixing portion 11. A accommodating chamber capable of accommodating a coolant is formed within the fixing portion 11. The insides of the pair of left and right extending portions 14 and 15 communicate with the accommodating chamber of the fixing portion 11, and accommodating chambers capable of housing a coolant are respectively formed in the insides of the pair of left and right extending portions 14 and 15.

In addition, the fixing portion 11 is provided on the opposite side from the surface of the ring-shaped cuff 7 tightly adhered to the tracheal opening, and is fixed to the ring-shaped cuff 7 in a state where a portion of the ring-shaped cuff 7 is inserted therein. More specifically, the fixing portion 11 is provided with a bottom portion 11a having the shape of a flat plate corresponding to the ring-shaped cuff body 7b, and a right sidewall 11b, left sidewall 11c, right base end wall 11d and right base end wall 11e rising from the peripheral edge of this bottom portion 11a. The right base end wall 11d extends towards the left side from the base end of the right sidewall 11b. The left base end wall 11e extends towards the right side from the base end of the left sidewall 11c. A gap S1 is formed between the right base end wall 11d and the left base end wall 11e to allow the outer tube 4a to pass through. The extending portion 14 extends towards the base end side from the right base end wall 11d and curves corresponding to the outer tube 4a. Similarly, the extending portion 15 extends towards the base end side from the left base end wall 11e and curves corresponding to the outer tube 4a.

The supply and evacuation tube 9 communicates with the inside of the extending portion 14 and extends towards the base end side from the extending portion 14. Similarly, the supply and evacuation tube 10 communicates with the inside of the extending portion 15 and extends towards the base end side from the extending portion 15. The leading ends of these supply and evacuation tubes 9 and 10 are arranged outside the human body J in a state where the ring-shaped cuff 7 is inserted to a predetermined insertion position. A coolant port not shown is provided on the leading end of each supply and evacuation tubes 9 and 10. The cooling cuff 8 inflates as a result of supplying coolant to the cooling cuff 8 through these coolant ports. The human body J (pharyngeal portion T) is cooled by carrying out heat exchange between coolant in the cooling cuff 8 and the human body J.

The following provides an explanation of a method for using the laryngeal mask.

First, with reference to FIG. 1, a gas in the ring-shaped cuff body 7b is evacuated through the gas supply and evacuation portion 7e of the ring-shaped cuff 7. As a result, the ring-shaped cuff body 7b is deflated. While in this state, the ring-shaped cuff 7 is introduced into the body through the oral cavity J2 from the leading end of the insertion tube body 4.

Figure 8:
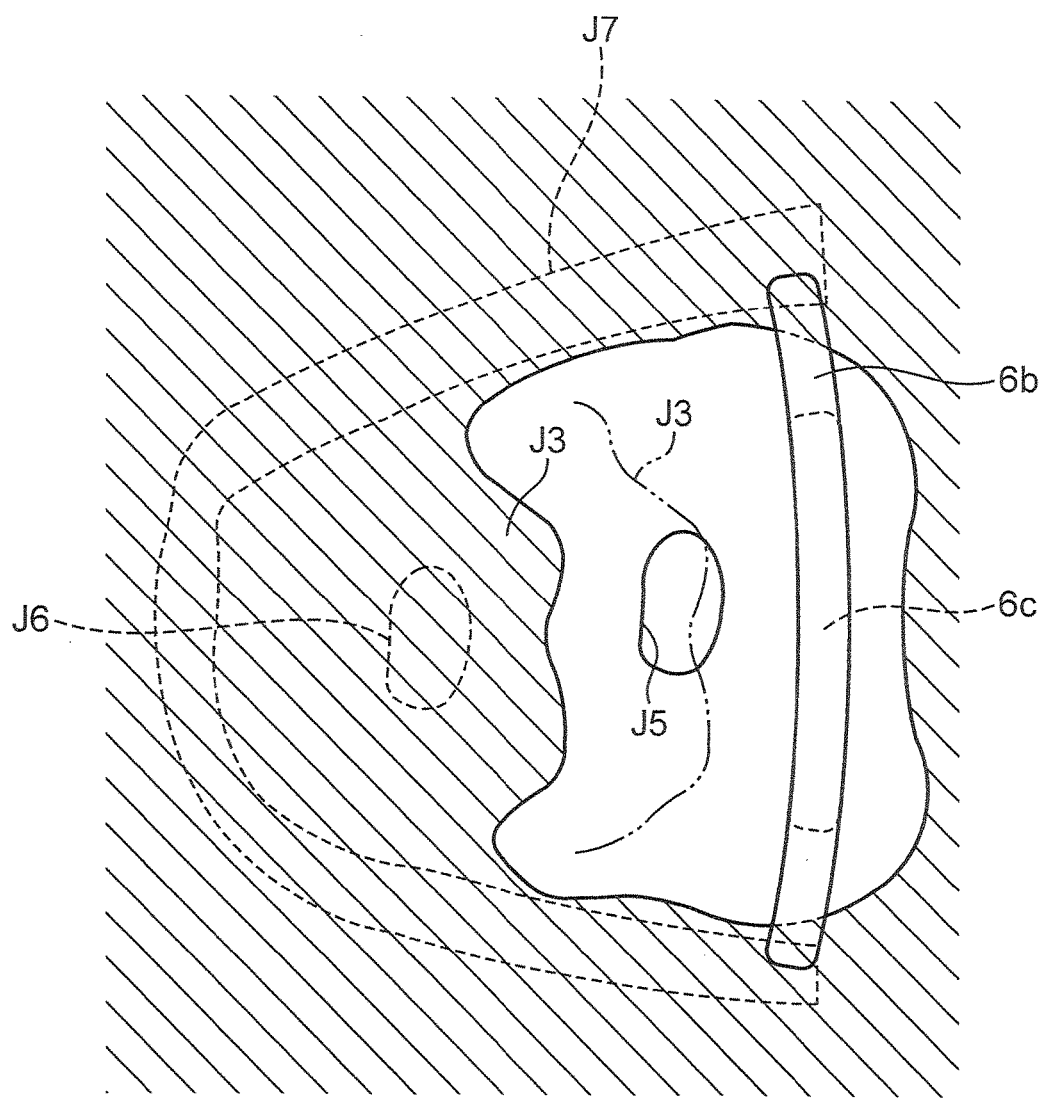
FIG. 8 is a cross-sectional view taken along line VIII-VIII of FIG. 7.

During the course of this insertion, space between the epiglottis J3 and the posterior wall of the pharyngeal portion T may be restricted by downward movement of the epiglottis J3 as indicated by the double-dot broken line of FIG. 8. In such a case, the ring-shaped cuff 7 can be inserted deeper by sliding the plate-shaped extending portion 6c of the positioning member 6 between the epiglottis J3 and the posterior wall of the pharyngeal portion T.

As the ring-shaped cuff 7 advances to a predetermined insertion position, the hyoid bone-contacting portions 6d and 6e of the positioning member 6 contact a site corresponding to the hyoid bone J7 as shown in FIGS. 7 and 8. The hyoid bone J7 has a U-shape so as to surround the pharyngeal portion T of the human body J from the anterior side and both the left and right sides. Consequently, the site in the pharyngeal portion T corresponding to the hyoid bone J7 is harder than the soft tissue in the vicinity of the first constricting portion J4. In addition, although not shown in the drawings, since the hyoid bone J7 is joined to tissue in the vicinity of the tracheal opening in the human body, there is little fluctuation in its position with respect to the tracheal opening. Thus, the ring-shaped cuff 7 can be accurately positioned at the predetermined insertion position by contacting the hyoid bone-contacting portions 6d and 6e with the hyoid bone J7. More specifically, the ring-shaped cuff 7 is positioned at the insertion position shown in FIG. 8 where the leading end of the ring-shaped cuff 7 (positioning member 6) is positioned below the branch of the esophagus J5 and the trachea J6 and slightly above the first constricting portion J4. Furthermore, since the present embodiment has the pair of left and right hyoid bone-contacting portions 6d and 6e, the laryngeal mask 1 can be restricted from inclination to the left or right with respect to the hyoid bone J7.

Next, the ring-shaped cuff body 7b is inflated at the insertion position. As a result, the esophagus J5 and the trachea J6 are blocked and the trachea J6 is isolated from the outside as shown in FIG. 9. While in this state, an artificial respirator is connected to the first connecting portion 5b of the connector 5. As a result, the airway of the human body is secured through the outer tube 4a as indicated by arrows Y1.

As has been explained above, the present embodiment has hyoid bone-contacting portions 6d and 6e that are capable of contacting the hyoid bone J7 from above, the hyoid bone being harder than soft tissue in the vicinity of the first constricting portion J4 and demonstrating little fluctuation in its positional relationship with the tracheal opening. Consequently, in comparison with the case of determining the insertion position of the outer tube 4a based on the presence or absence of a sensation felt when contact is made with the first constricting portion J4, the outer tube 4a can be accurately positioned at the predetermined insertion position.

Thus, according to the present embodiment, an airway can be reliably secured by a simple procedure of inserting the outer tube 4a into the pharyngeal portion T of a patient.

In the present embodiment, the two hyoid bone-contacting portions 6d and 6e protruding to both the left and right sides from the outer tube 4a are provided. The hyoid bone J7 is arranged on both the left and right sides of the pharyngeal portion T as previously described. Consequently, by contacting the two left and right hyoid bone-contacting portions 6d and 6e with the hyoid bone J7, inclination in the right-and-left direction of the laryngeal mask 1 can be inhibited in a state where the laryngeal mask 1 is inserted to the predetermined insertion position. Thus, an airway can be more accurately secured by the present embodiment.

In the present embodiment, hyoid bone-contacting portions are formed on the positioning member 6. As a result, differing from the case of forming the hyoid bone-contacting portions 6d and 6e as a portion of the outer tube 4a, the hardness of the hyoid bone-contacting portions 6d and 6e can be freely adjusted independent of the outer tube 4a. In the present embodiment, the hyoid bone-contacting portions 6d and 6e are harder than the ring-shaped cuff body 7b. Consequently, in comparison with the case of forming the hyoid bone-contacting portions on the ring-shaped cuff 7, the ring-shaped cuff 7 can be positioned more accurately with respect to the hyoid bone J7. Furthermore, if the hardness of the hyoid bone-contacting portions 6d and 6e is made to be harder than the outer tube 4a having hardness greater than that of the ring-shaped cuff 7, the ring-shaped cuff 7 can be positioned more accurately.

In the present embodiment, the plate-shaped extending portion 6c extending farther towards the leading end side than the leading end of the outer tube 4a is formed in the positioning member 6 having hardness greater than that of the outer tube 4a. Consequently, the leading end of the outer tube 4a can be reliably inserted downward beyond the epiglottis J3 by sliding this extending portion 6c between the epiglottis J3 and the posterior wall of the pharyngeal portion T.

In the present embodiment, the hyoid bone-contacting portions 6d and 6e are formed between the extending portion 6c and the wide portion 6b. Consequently, by advancing insertion of the outer tube 4a so that the extending portion 6c slides between the epiglottis J3 and the posterior wall of the pharyngeal portion T, the hyoid bone-contacting portions 6d and 6e positioned on the base end side of this extending portion 6c contact a site corresponding to the hyoid bone J7. Thus, in the present embodiment, both insertion ease and positioning ease can be realized for the laryngeal mask 1.

The present embodiment has the cooling portion 3 that is able to tightly adhere to the pharyngeal portion T in a state where the ring-shaped cuff 7 is inflated. Consequently, the pharyngeal portion T can be cooled as a result of the cooling portion 3 tightly adhering to the pharyngeal portion T in a state where the ring-shaped cuff 7 is inflated. Here, since blood vessels that supply blood to the brain are concentrated in the vicinity of the pharyngeal portion T, cooling of these blood vessels makes it possible to inhibit the occurrence of so-called ischemic neuronal damage in which neuronal cells die as a result of a shortage of oxygen supplied to the brain during respiratory function or circulatory function failure like that occurring during cardiac arrest.

The present embodiment has a cooling cuff 8, which is capable of being inflated and deflated by supplying and evacuating a coolant, and two supply and evacuation tubes 9 and 10 capable of supplying and evacuating the coolant in the cooling cuff 8. Consequently, the coolant can be circulated by introducing the coolant into the cooling cuff 8 through one of the supply and evacuation tubes 9 and evacuating the coolant from the cooling cuff 8 through the other supply and evacuation tube 10. Thus, the pharyngeal portion T can be cooled efficiently.

Furthermore, although an explanation has been provided of the present embodiment in which the laryngeal mask 1 is provided with the cooling portion 3, the cooling portion 3 is not essential. More specifically, only the mask body 2 shown in FIG. 2 can be used for the laryngeal mask 1.

Furthermore, inventions having the configurations indicated below are mainly included in the specific embodiment as previously explained.

In order to solve the problems, the present invention provides a laryngeal mask for securing an airway of a patient, provided with: an insertion tube having a base end in which is formed a connecting portion capable of being connected to an artificial respirator, a leading end in which is formed a ventilation opening, and a communication passage formed therein that communicates between the connecting portion and the ventilation opening, a ring-shaped cuff which is attached to the leading end of the insertion tube so as to surround the ventilation opening, and is capable of tightly adhering to a tracheal opening of a patient trachea as a result of inflating in a state where the ring-shaped cuff is inserted to a predetermined insertion position in the patient, and at least one hyoid bone-contacting portion that protrudes laterally from the insertion tube so as to contact a site, in a pharyngeal portion of the patient, corresponding to a hyoid bone of the patient in a state where the ring-shaped cuff is inserted to the insertion position.

Figure 6:
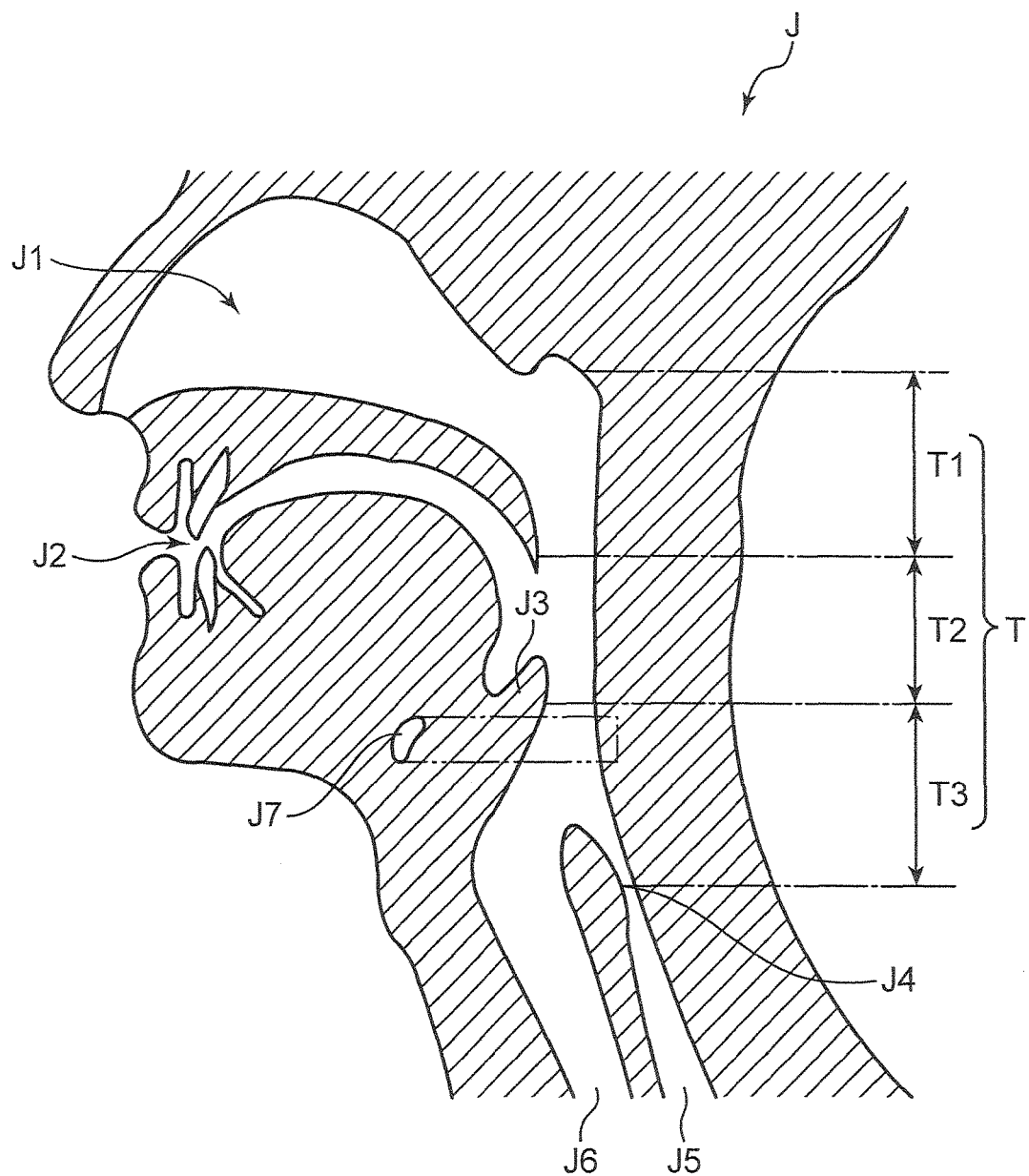
FIG. 6 is a side cross-sectional view showing the structure of a human body.

As shown in FIGS. 6 and 8, the hyoid bone J7 is a bone having a U-shape so as to surround the pharyngeal portion T of the human body J from the anterior side and from both the left and right sides. Consequently, the site in the pharyngeal portion T corresponding to the hyoid bone is harder than soft tissue in the vicinity of the first constricting portion J4. In addition, although not shown in the drawings, since the hyoid bond J7 is joined by ligaments to tissue in the vicinity of the trachea opening, there is little fluctuation in its position relative to the tracheal opening. The present invention has a hyoid bone-contacting portion capable of contacting the hyoid bone J7 from above, the hyoid bone J7 being harder than soft tissue in the vicinity of the first constricting portion J4 and demonstrating little fluctuation in its positional relationship with the tracheal opening. Consequently, in comparison with the case of determining the insertion position based on the presence or absence of contact with the first constricting portion J4, the insertion tube can be accurately positioned at a predetermined insertion position.

Thus, according to the present invention, an airway can be reliably secured by a simple procedure of inserting an insertion tube into the pharyngeal portion of a patient.

Furthermore, "contacting a site corresponding to the hyoid bone" refers to contacting the hyoid bone with soft tissue interposed between the hyoid bone-contacting portion and hyoid bone in the pharyngeal portion. In addition, "from above" refers to an orientation in which the oral cavity is on the upper side while the esophagus is on the lower side based on the location of the hyoid bone.

In the laryngeal mask, the at least one hyoid bone-contacting portion preferably includes two hyoid bone-contacting portions that protrude to both left and right sides from the insertion tube in a state where the ring-shaped cuff is inserted to the insertion position.

In this aspect, the two hyoid bone-contacting portions are provided protruding to both the left and right sides from the insertion tube. The hyoid bone J7 is arranged on both the left and right sides of the pharyngeal portion T as previously described. Consequently, inclination of the laryngeal mask to the left and right in a state where the insertion tube is inserted can be inhibited by allowing the two left and right hyoid bone-contacting portions to contact the hyoid bone. Thus, according to this aspect, an airway can be secured more accurately.

The laryngeal mask is preferably further provided with a positioning member fixed to the insertion tube, and the at least one hyoid bone-contacting portion is formed on the positioning member.

In this aspect, a hyoid bone-contacting portion is formed on the positioning member. As a result, differing from the case in which a hyoid bone-contacting portion is formed as a portion of an insertion tube, hardness of the hyoid bone-contacting portion can be freely adjusted independent of the insertion tube. Consequently, by making the hardness of the hyoid bone-contacting portion to be greater than that of the insertion tube, the position of the hyoid bone-contacting portion relative to the hyoid bone, or in other words, the insertion position of the ring-shaped cuff, can be accurately determined.

In the laryngeal mask, the positioning member preferably has an extending portion in the shape of a flat plate that extends farther towards the leading end side than the leading end of the insertion tube.

The epiglottis J3 is present in the upper portion of the trachea J6 as shown in FIGS. 6 and 8 for preventing entry of food into the trachea J6. When the epiglottis J3 moves as indicated by the double-dot broken line of FIG. 8, the area of the passage within the pharyngeal portion T becomes narrow in the anteroposterior direction. Here, in this aspect, an extending portion in the shape of a flat plate that extends farther towards the leading end side than the leading end of the insertion tube is formed on the poisoning member. Consequently, the leading end of the insertion tube can be reliably inserted downward beyond the epiglottis J3 by sliding this extending portion between the epiglottis J3 and the posterior wall of the pharyngeal portion T.

Furthermore, in the prior art, an insertion tube was inserted between the epiglottis and posterior wall of the pharyngeal portion by twisting. Consequently, there were cases in which the leading end of the insertion tube mistakenly entered the trachea. In this aspect, however, since the extending portion can be slid between the epiglottis and posterior wall of the pharyngeal portion as previously described, mistakenly inserting the insertion tube into the trachea as a result of twisting as in the prior art can be inhibited.

In the laryngeal mask, the positioning member is provided with the extending portion and a wide portion that is provided on a base end side of the extending portion and has a width greater than that of the extending portion, and a portion of the wide portion that protrudes in the direction of width from the extending portion preferably forms the at least one hyoid bone-contacting portion.

In this aspect, the portion of the wide portion protruding in the direction of width from the extending portion forms the hyoid bone-contacting portion. Consequently, by advancing insertion of the insertion tube so as to slide the extending portion between the epiglottis and the posterior wall of the pharyngeal portion as previously described, the hyoid bone-contacting portion positioned on the base end side of this extending portion contacts a site corresponding to the hyoid bone. Thus, in this aspect, both insertion ease and positioning ease are realized for the laryngeal mask.

The laryngeal mask is preferably further provided with a cooling portion that is able to tightly adhere to and cool the pharyngeal portion of the patient in a state where the ring-shaped cuff is inflated at the predetermined insertion position.

In this aspect, the laryngeal mask has a cooling portion capable of tightly adhering to the pharyngeal portion in a state where the ring-shaped cuff is inflated. Consequently, the pharyngeal portion can be cooled as a result of the cooling portion tightly adhering to the pharyngeal portion in a state where the ring-shaped cuff is inflated. Here, since blood vessels that supply blood to the brain are concentrated in the vicinity of the pharyngeal portion, cooling of these blood vessels makes it possible to cool the brain by means of the blood within each of these blood vessels. As a result of cooling the brain in this manner, it is possible to inhibit the occurrence of so-called ischemic neuronal damage in which neuronal cells die as a result of a shortage of oxygen supplied to the brain during respiratory function or circulatory function failure like that occurring during cardiac arrest. Although a cuff capable of housing a coolant in the manner to be subsequently described, for example, may be used for the cooling portion, a member formed from a material having high specific heat can also be used.

In the laryngeal mask, the cooling portion is preferably provided with a cooling cuff that can be inflated or deflated corresponding to supply and evacuation of a coolant, and two coolant tubes capable of supplying and evacuating coolant to and from the cooling cuff.

This aspect is provided with a cooling cuff that can be inflated by supplying a coolant, and two coolant tubes capable of supplying and evacuating coolant to and from the cooling cuff. Consequently, the coolant can be circulated by introducing the coolant into the cooling cuff through one of the coolant tubes and evacuating the coolant from the cooling cuff through the other coolant tube. Thus, the pharyngeal portion can be cooled efficiently.

According to the present invention, an airway can be accurately secured by a simple procedure.

The invention claimed is:

1. A laryngeal mask for securing an airway of a patient, comprising:
   an insertion tube including a base end with a connecting portion configured to be connected to an artificial respirator, a leading end spaced from the base end in an insertion direction and a ventilation opening in the leading end, and a communication passage formed therein that communicates between the connecting portion and the ventilation opening;
   a positioning member fixed to the insertion tube, the positioning member having an extending portion defining a flat plate that extends farther in the insertion direction than the leading end of the insertion tube;
   a ring-shaped cuff attached to the leading end of the insertion tube so as to surround the ventilation opening, and being capable of tightly adhering to a tracheal opening of a patient trachea as a result of inflating in a state where the ring-shaped cuff is inserted to a predetermined insertion position in the patient, and the ring-shaped cuff being provided with a bottom portion in the shape of a flat plate corresponding to the positioning member, and a ring-shaped cuff body provided over an entire periphery of a peripheral edge of the bottom portion, the ring-shaped cuff body having an inner peripheral surface facing toward the leading end of the insertion tube and an outer peripheral surface facing out and away from the leading end of the insertion tube, a first surface on one side of the ring-shaped cuff body being configured to adhere tightly to the tracheal opening of the trachea over the entire periphery thereof, the extending portion of the positioning member having a leading end introduced to an inside of the ring-shaped cuff body through a hole formed in the bottom portion, and a base side portion provided on a base end side of the leading end of the positioning member, the base side portion being disposed on a side of the ring-shaped cuff body opposite the first surface and extending along the bottom portion of the ring-shaped cuff; and
   at least one hyoid bone-contacting portion formed on the positioning member and protruding laterally from the insertion tube so as to contact from above a site in a pharyngeal portion of the patient corresponding to a hyoid bone of the patient in a state where the ring-shaped cuff is inserted to the insertion position, wherein
   the ring-shaped cuff body has a leading end disposed farther in the insertion direction than both the leading end of the insertion tube and the leading end of the extending portion so that the leading end of the extending portion is opposed to the inner peripheral surface of the ring-shaped cuff body at the leading end of the ring-shaped cuff body, and
   the positioning member has a hardness higher than the ring-shaped cuff.

2. The laryngeal mask according to claim 1, wherein the at least one hyoid bone-contacting portion includes two hyoid bone-contacting portions that protrude to both left and right sides from the insertion tube in a state where the ring-shaped cuff is inserted to the insertion position.

3. The laryngeal mask according to claim 1, wherein the positioning member has a wide portion provided on a base end side of the extending portion and has a width greater than that of the extending portion, and
   a portion of the wide portion that protrudes in a width direction from the extending portion forms the at least one hyoid bone-contacting portion.

4. The laryngeal mask according to claim 1, further comprising a cooling portion that is able to tightly adhere to and cool the pharyngeal portion of the patient in a state where the ring-shaped cuff is inflated at the predetermined insertion position.

5. The laryngeal mask according to claim 4, wherein the cooling portion has a cooling cuff that can be inflated or deflated corresponding to supply and evacuation of a coolant, and two coolant tubes capable of supplying and evacuating coolant to and from the cooling cuff.

6. The laryngeal mask according to claim 1, wherein:
   the ring-shaped cuff is provided with a tube attaching portion for attaching the insertion tube and a gas supply and evacuation portion for supplying and evacuating a gas to and from the ring-shaped cuff body;
   the at least one hyoid bone-contacting portion of the positioning member is configured to contact a site corresponding to the hyoid bone by insertion of the at least one hyoid bone contacting portion into a predetermined insertion position in a state where the ring-shaped cuff body is deflated, and
   the ring-shaped cuff body is configured to be inflated at the insertion position by supply of gas into the ring-shaped cuff body through the gas supply and evacuation portion.

* * * * *